US012066416B2

(12) United States Patent
Hattori et al.

(10) Patent No.: US 12,066,416 B2
(45) Date of Patent: Aug. 20, 2024

(54) ARITHMETIC DEVICE, ARITHMETIC METHOD, AND GAS DETECTION SYSTEM

(71) Applicant: TAIYO YUDEN CO., LTD., Tokyo (JP)

(72) Inventors: Masashi Hattori, Tokyo (JP); Kenichi Shimomai, Tokyo (JP); Yosuke Onda, Tokyo (JP)

(73) Assignee: TAIYO YUDEN CO., LTD., Tokyo (JP)

( * ) Notice: Subject to any disclaimer, the term of this patent is extended or adjusted under 35 U.S.C. 154(b) by 330 days.

(21) Appl. No.: 17/605,543

(22) PCT Filed: Apr. 17, 2020

(86) PCT No.: PCT/JP2020/016840
§ 371 (c)(1),
(2) Date: Oct. 21, 2021

(87) PCT Pub. No.: WO2020/218179
PCT Pub. Date: Oct. 29, 2020

(65) Prior Publication Data
US 2022/0236225 A1   Jul. 28, 2022

(30) Foreign Application Priority Data
Apr. 22, 2019   (JP) ................ 2019-081287

(51) Int. Cl.
*G01N 33/00*   (2006.01)
*G01N 1/40*   (2006.01)
(Continued)

(52) U.S. Cl.
CPC ........... *G01N 33/0027* (2013.01); *G01N 1/40* (2013.01); *G01N 5/02* (2013.01); *G01N 29/02* (2013.01);
(Continued)

(58) Field of Classification Search
CPC ............ G01N 5/025; G01N 5/02; G01N 5/00; G01N 29/036; G01N 29/02;
(Continued)

(56) References Cited

U.S. PATENT DOCUMENTS 5,065,140 A * 11/1991 Neuburger ......... G01N 33/0062
73/23.31
7,216,527 B2 * 5/2007 Imoto ................ G01N 33/0009
73/1.06
(Continued)

FOREIGN PATENT DOCUMENTS

CN   107703187 A   2/2018
CN   107870183 A   4/2018
(Continued)

OTHER PUBLICATIONS

Japanese Office Action dated Oct. 3, 2023 in a counterpart Japanese patent application No. 2023-003393. (A machine translation (not reviewed for accuracy) attached.).
(Continued)

*Primary Examiner* — Judy Nguyen
*Assistant Examiner* — James Split
(74) *Attorney, Agent, or Firm* — CHEN YOSHIMURA LLP

(57) ABSTRACT

[Object] To provide an arithmetic device, an arithmetic method, and a gas detection system that are capable of easily correcting deterioration over time of a detection element.
[Solving Means] The arithmetic device includes a calculation unit. The calculation unit calculates a correction coefficient from a detection element that causes a resonant
(Continued)

frequency change by adsorption of gas on the basis of a resonant frequency change amount associated with a humidity change of the detection element in a degraded state and a resonant frequency change amount associated with a humidity change of the detection element in an initial state that was acquired in advance, and corrects the resonant frequency change amount of the detection element in the degraded state by using the correction coefficient.

8 Claims, 10 Drawing Sheets

(51) Int. Cl.
G01N 5/02 (2006.01)
G01N 29/02 (2006.01)
G01N 29/036 (2006.01)
G01N 29/22 (2006.01)
G01N 29/44 (2006.01)

(52) U.S. Cl.
CPC ......... *G01N 29/036* (2013.01); *G01N 29/222* (2013.01); *G01N 29/4463* (2013.01); *G01N 2291/014* (2013.01); *G01N 2291/021* (2013.01); *G01N 2291/0215* (2013.01); *G01N 2291/0256* (2013.01); *G01N 2291/106* (2013.01)

(58) Field of Classification Search
CPC ......... G01N 2291/014; G01N 29/4463; G01N 33/0027; G01N 33/0009; G01N 33/0006; G01N 33/0004; G01N 2291/021; G01N 2291/0215; G01N 2291/0212; G01N 33/0031; G01N 29/2443; G01N 29/2437; G01N 2291/0256
See application file for complete search history.

(56) References Cited

U.S. PATENT DOCUMENTS

| | | | |
|---|---|---|---|
| 10,444,192 B2 * | 10/2019 | Takasu | ................ G01N 29/036 |
| 2018/0045682 A1 | 2/2018 | Hattori | |
| 2018/0088088 A1 | 3/2018 | Shimomai et al. | |
| 2018/0266995 A1 | 9/2018 | Hattori et al. | |
| 2019/0056370 A1 | 2/2019 | Yamasaki et al. | |
| 2022/0236225 A1 | 7/2022 | Hattori et al. | |

FOREIGN PATENT DOCUMENTS

| | | | | |
|---|---|---|---|---|
| CN | 108627413 A | | 10/2018 | |
| GB | 2285508 A | * | 7/1995 | ............. G01N 17/04 |
| JP | H07-174673 A | | 7/1995 | |
| JP | H07-225184 A | | 8/1995 | |
| JP | H10-90152 A | | 4/1998 | |
| JP | 2014145608 A | * | 8/2014 | |
| JP | 2018-048930 A | | 3/2018 | |
| JP | 2018-155576 A | | 10/2018 | |
| JP | 2020-176989 A1 | | 10/2020 | |
| JP | 2002-286668 A | | 10/2021 | |
| WO | 2017/145933 A1 | | 8/2017 | |

OTHER PUBLICATIONS

International Search Report (ISR) issued in PCT/JP2020/016840 mailed in Jul. 2020.
Written Opinion (PCT/ISA/237) issued in PCT/JP2020/016840 mailed in Jul. 2020. (Concise Explanation of Relevance: This Written Opinion considers that the claims are not described by or obvious over the references Nos. 2-5 cited in ISR above.).
English translation of Written Opinion (PCT/ISA/237) issued in PCT/JP2020/016840 mailed in Jul. 2020.
Chinese Office Action dated Dec. 28, 2023 in a counterpart Chinese patent application No. 202080030845.9. (A machine translation (not reviewed for accuracy) attached.).

* cited by examiner

FIG.3
(A)
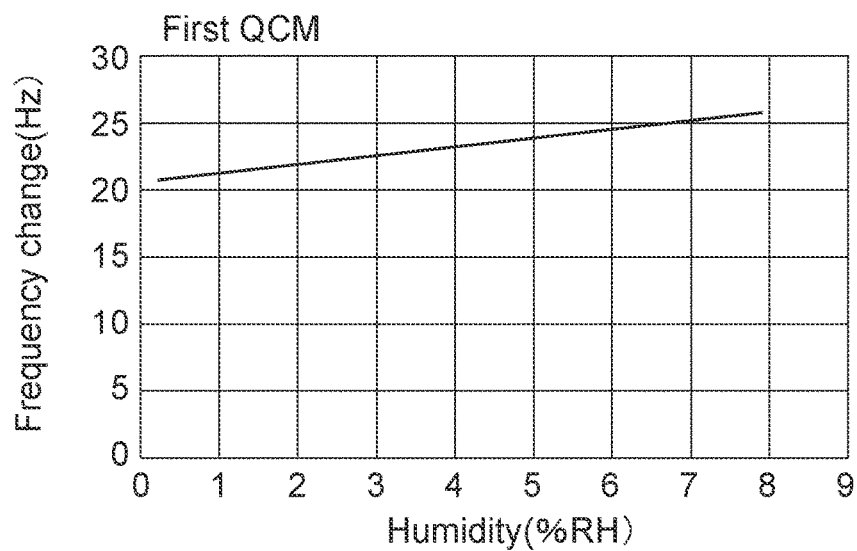
(B)
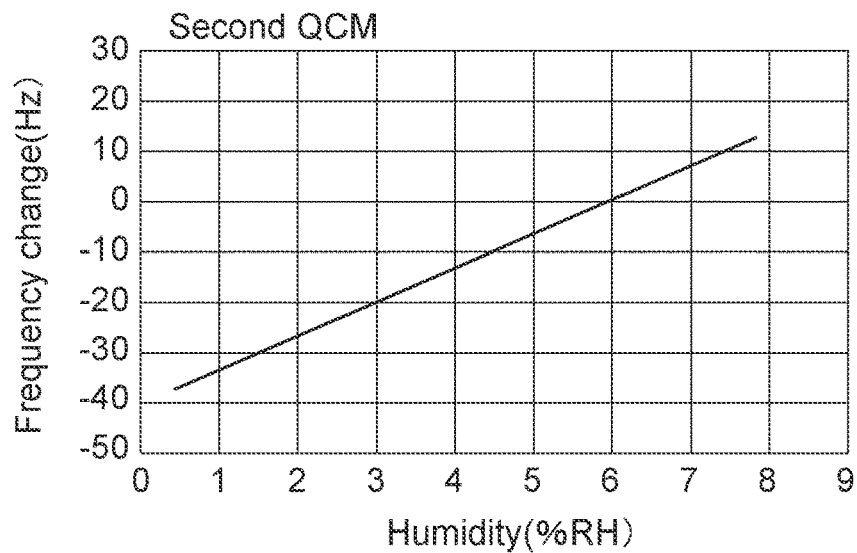
(C)
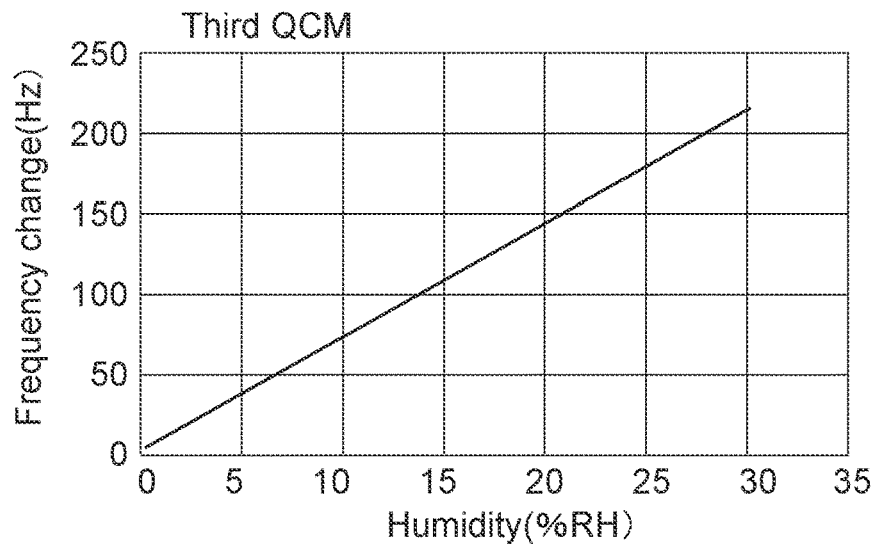

FIG.4
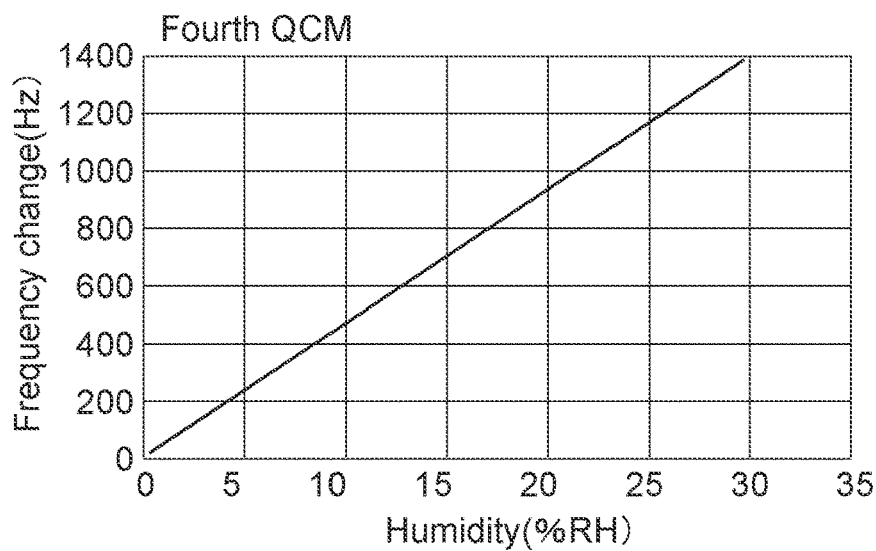
(A)
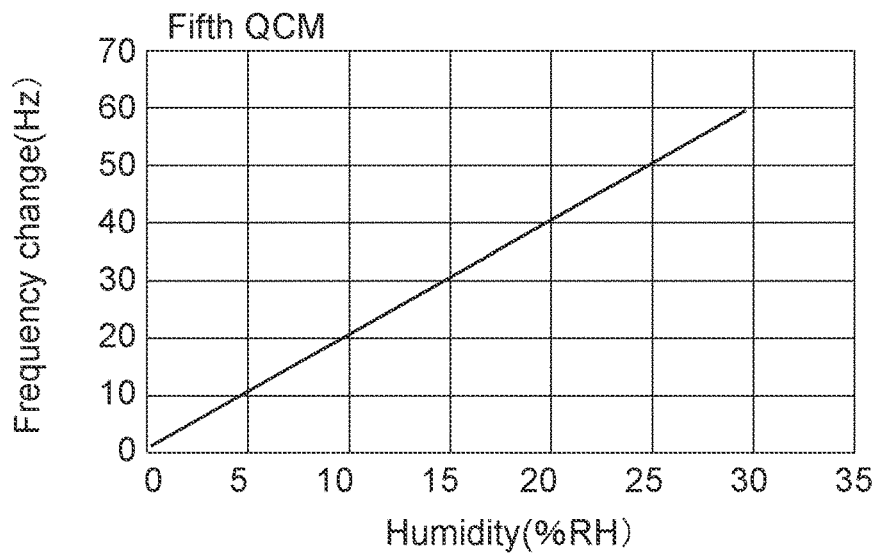
(B)
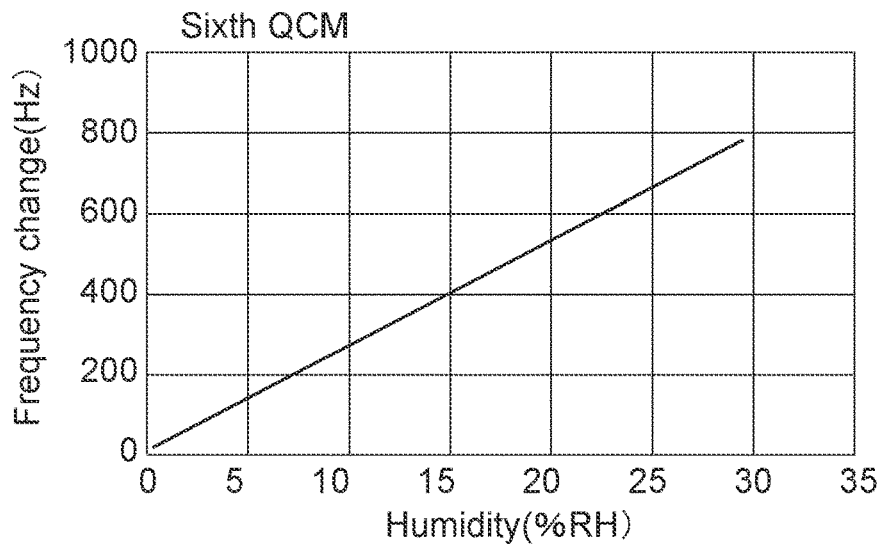
(C)

| | First QCM | Second QCM | Third QCM | Fourth QCM | Fifth QCM | Sixth QCM |
|---|---|---|---|---|---|---|
| Frequency change associated with humidity fluctuation in initial state (Hz/%RH) | −2.4 | −9.2 | −30.1 | −25.1 | −26.8 | −3.7 |
| Frequency change associated with humidity fluctuation after deterioration over time (Hz/%RH) | −1 | −7 | −15 | −18 | −13 | −2 |
| Correction coefficient (Rc) | 2.4 | 1.3 | 2.0 | 1.4 | 2.1 | 1.9 |
| Frequency change of ethanol (100 ppm) in initial state (Hz) | 20 | 70 | 200 | 210 | 350 | 120 |
| Frequency change of ethanol (100 ppm) after deterioration over time (Hz) | 9 | 55 | 95 | 145 | 176 | 64 |
| Frequency change after correction (Hz) | 22 | 72 | 191 | 202 | 363 | 118 |
| Output coincidence rate (%) | 108 | 103 | 95 | 96 | 104 | 99 |

FIG.5

ARITHMETIC DEVICE, ARITHMETIC METHOD, AND GAS DETECTION SYSTEM

TECHNICAL FIELD

The present invention relates to an arithmetic device, an arithmetic method, and a gas detection system relating to gas detection.

BACKGROUND ART

In order to distinguish an odor that is an aggregate of a plurality of gas components, an odor sensor in which adsorption films having a plurality of different chemical properties are arrayed into a multi-array sensor and an odor is patterned has been actively developed in recent years. Use of such an odor sensor makes it possible to distinguish between a pleasant odor and an unpleasant odor. The application of the odor sensor to the field that has been organoleptically evaluated by a person until now has begun to be examined, such as environment management in a room or a vehicle, process management in a factory, or environment monitoring for detecting an initial fire or an offensive odor that adversely affects a human body.

For example, a detection element including an adsorption film provided on a crystal oscillator is used as the odor sensor. Since the resonant frequency of the crystal oscillator decreases in proportion to the weight of the gas adsorbed on the adsorption film, the gas can be detected on the basis of the amount of change in the resonant frequency. Thus, a decrease in the sensitivity level due to the deterioration over time of the adsorption film that adsorbs odor substances affects the reliability of the odor sensor. The deterioration of the adsorption film due to the deterioration over time is mainly caused by the fact that odor components adsorbed at the time of using the sensor cannot be desorbed from the adsorption film, continue to stay on the adsorption film, and are thus deposited.

Patent Literature 1 discloses that, in order to reduce factors that may become detection errors before or after the detection of an odor by a detection unit, the inside of a container in which a detection element is contained is subjected to a refresh process by performing degassing or deodorization, and the detection unit is initialized.

Further, in order to remove odor components adsorbed on the adsorption film, there is also a method in which heat treatment is performed to refresh the adsorption film, for example, when the adsorption film is an organic film.

CITATION LIST

Patent Literature

Patent Literature 1: WO 2017/145933

Disclosure of Invention

Technical Problem

In Patent Literature 1, although the detection unit is initialized by the refresh process to correct the deterioration over time of the detection element, there is a case where odor components that are hardly desorbed at normal temperature even by the refresh process are adsorbed on the adsorption film of the detection element. In such a case, it is the simplest to replace the detection unit, but there is a problem that labor and cost are required.

In addition, refreshing by heat treatment requires several hours, and gas detection cannot be performed during refreshing, resulting in poor time efficiency. In addition, thermal decomposition or thermal degradation of the adsorption film may occur due to heat treatment, which makes it difficult to perform gas detection with stable detection sensitivity.

In view of the above circumstances, it is an object of the present invention to provide an arithmetic device, an arithmetic method, and a gas detection system that are capable of easily correcting deterioration over time of a detection element.

Solution to Problem

In order to achieve the above object, an arithmetic device according to an embodiment of the present invention includes a calculation unit.

The calculation unit calculates a correction coefficient on the basis of a resonant frequency change amount associated with a humidity change of a detection element in a degraded state and a resonant frequency change amount associated with a humidity change of the detection element in an initial state and acquired in advance, the detection element causing a resonant frequency change by adsorption of gas, and corrects the resonant frequency change amount of the detection element in the degraded state by using the correction coefficient.

According to such a configuration of the present invention, the ratio of adsorption sites capable of adsorption in the adsorption sites of the adsorption film excluding adsorption sites occupied by odor components that are not desorbed can be estimated on the basis of the resonant frequency change amount associated with the humidity change of the detection element in each of the initial state and the degraded state. The ratio of the adsorption sites capable of adsorption is calculated as a correction coefficient, and the resonant frequency change amount is corrected using the correction coefficient, so that it is possible to convert the resonant frequency amount into a resonant frequency amount of substantially the same output level as that in the initial state. As a result, it is possible to detect the gas at substantially the same sensitivity level as that in the initial state, and it is possible to easily correct the deterioration over time of the detection element.

The arithmetic device may further include a storage unit that stores the resonant frequency change amount associated with the humidity change of the detection element in the initial state.

The storage unit may store the correction coefficient.

The detection element may include an oscillator, and an adsorption film that is provided on the oscillator and adsorbs the gas. The storage unit may store a resonant frequency change amount associated with a humidity change of each of a plurality of detection elements in an initial state, the plurality of detection elements having different types of the adsorption film.

The arithmetic device may further include a determination unit that determines a lifetime of the detection element on the basis of a difference between a resonant frequency detected from the detection element in the degraded state at which a zero-point gas has arrived, and a resonant frequency detected from the detection element in the initial state at which the zero-point gas has arrived, and acquired in advance.

In order to achieve the above object, an arithmetic method according to an embodiment of the present invention includes: calculating a resonant frequency change amount associated with a humidity change of a detection element in a degraded state, the detection element causing a resonant frequency change by adsorption of gas; calculating a correction coefficient on the basis of the resonant frequency change amount associated with the humidity change of the detection element in the degraded state and a resonant frequency change amount associated with a humidity change of the detection element in an initial state and acquired in advance; and correcting the resonant frequency change amount of the detection element in the degraded state by using the correction coefficient.

The calculating the resonant frequency change amount associated with the humidity change of the detection element may be performed on the basis of resonant frequencies detected by the detection element at which a zero-point gas and a gas having a humidity different from a humidity of the zero-point gas have arrived.

The zero-point gas may be a dehumidified and deodorized gas.

A lifetime of the detection element may be determined on the basis of a difference between a resonant frequency detected from the detection element in the degraded state at which the zero-point gas has arrived, and a resonant frequency detected from the detection element in the initial state at which the zero-point gas has arrived, and acquired in advance.

In order to achieve the above object, a gas detection system according to an embodiment of the present invention includes a gas sensor and an arithmetic device.

The gas sensor includes a detection element that causes a resonant frequency change by adsorption of gas.

The arithmetic device includes a calculation unit that calculates a correction coefficient on the basis of a resonant frequency change amount associated with a humidity change of the detection element in a degraded state and a resonant frequency change amount associated with a humidity change of the detection element in an initial state and acquired in advance, and corrects the resonant frequency change amount of the detection element in the degraded state by using the correction coefficient.

The gas sensor may include a first flow path that includes dehumidification and deodorization means disposed therein and guides detection target gas having passed through the dehumidification and deodorization means to the detection element, a second flow path that includes deodorization means disposed therein and guides the detection target gas having passed through the deodorization means to the detection element, and a third flow path directly guides the detection target gas to the detection element.

Advantageous Effects of Invention

As described above, according to the present invention, it is possible to easily correct deterioration over time of a detection element.

BRIEF DESCRIPTION OF DRAWINGS

FIG. 3 is a diagram showing a resonant frequency change with respect to the humidity of each QCM constituting a part of the gas sensor.

FIG. 4 is a diagram showing a resonant frequency change with respect to the humidity of each different QCM constituting a part of the gas sensor.

FIG. 5 is for describing a gas detection method in each QCM in the gas detection system.

MODE(S) FOR CARRYING OUT THE INVENTION

Hereinafter, embodiments of the present invention will be described with reference to the drawings.

In the following description, a QCM (quartz crystal microbalance) and an adsorption film, which are not yet subjected to odor detection, will be referred to as a QCM in an initial state and an adsorption film in an initial state, respectively. A QCM and an adsorption film after deterioration over time, which are subjected to odor detection and are obtained after a certain period of time has elapsed, will be referred to as a QCM in a degraded state and an adsorption film in a degraded state, respectively, for the purpose of convenience.

First Embodiment

Figure 1:
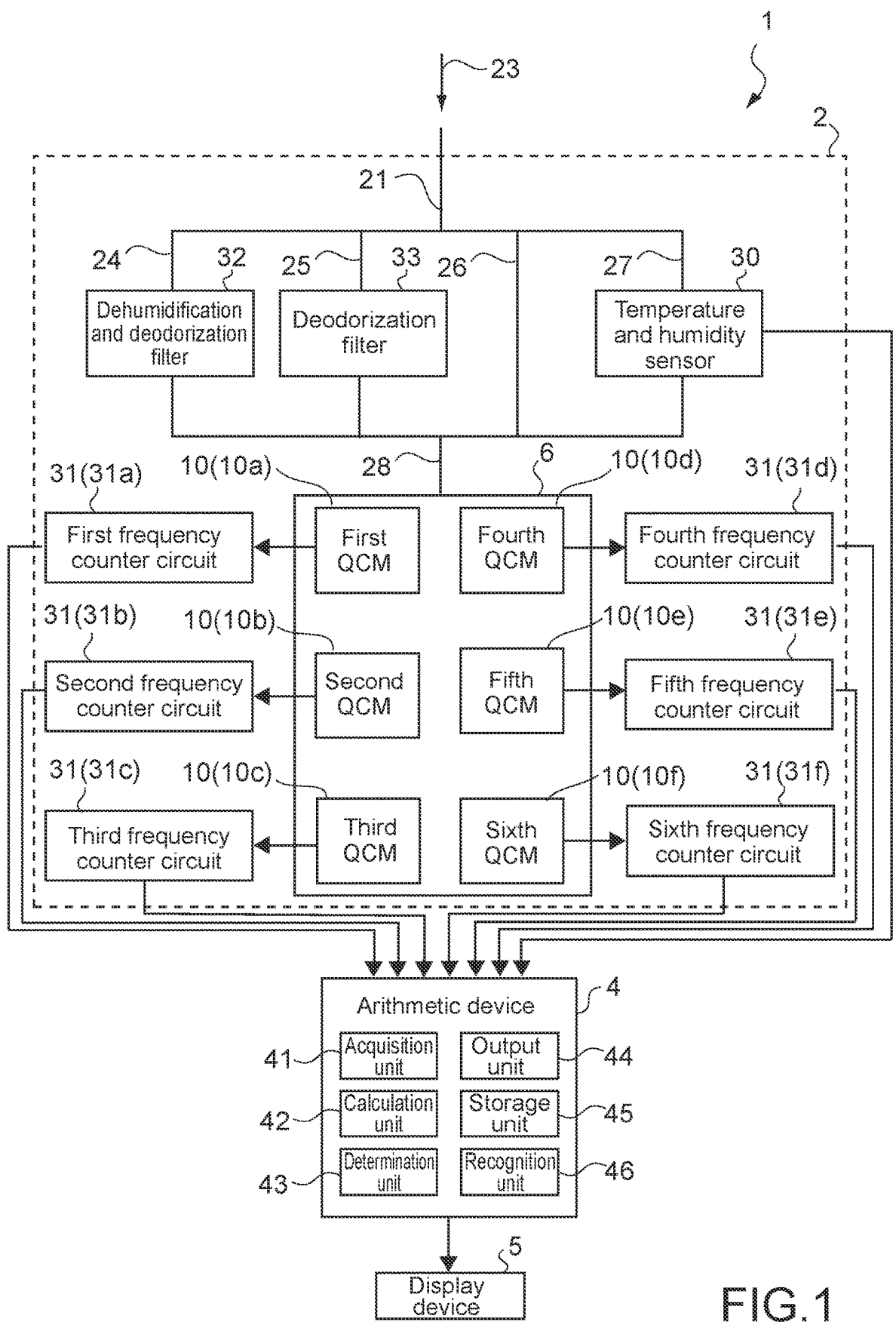
FIG. 1 is a schematic diagram showing a configuration of a gas detection system according to a first embodiment of the present invention.

FIG. 1 is a schematic diagram of a gas detection system 1 according to a first embodiment.

As shown in FIG. 1, the gas detection system 1 includes a gas sensor 2, an arithmetic device 4, and a display device 5.

As shown in FIG. 1, the gas sensor 2 includes an intake port 21, four flow paths of a first flow path 24, a second flow path 25, a third flow path 26, and a fourth flow path 27, and a fifth flow path 28 that is a single flow path into which the gas having passed through the four flow paths 24 to 27 flows.

The intake port 21 takes in detection target gas 23 from the outside.

The gas taken in from the intake port 21 can be guided to at least one of the four flow paths 24 to 27.

Each of the flow paths 24 to 27 is configured to guide the detection target gas 23 to a multi-array sensor 6 disposed on the fifth flow path 28.

It is possible to introduce the gas into each of the flow paths 24 to 27 mechanically at a constant flow rate using a fan, a pump, or the like (not shown). This makes it possible to cancel a disturbance factor caused by a pressure change due to a difference in flow rate or the like. Further, a valve (not shown) is provided in each of the flow paths 24 to 27, and the presence or absence of introduction of gas from the outside to each of the flow paths 24 to 27 can be controlled by opening or closing the valve.

As shown in FIG. 1, the gas sensor 2 includes a dehumidification and deodorization filter 32, a deodorization filter 33, a temperature and humidity sensor 30, the multi-array sensor 6, a first frequency counter circuit 31a, a second frequency counter circuit 31b, a third frequency counter circuit 31c, a fourth frequency counter circuit 31d, a fifth frequency counter circuit 31e, and a sixth frequency counter circuit 31f.

If it is not necessary to distinguish between the first frequency counter circuit 31a, the second frequency counter circuit 31b, the third frequency counter circuit 31c, the fourth frequency counter circuit 31d, the fifth frequency counter circuit 31e, and the sixth frequency counter circuit 31f in particular, they may be referred to as frequency counter circuit 31 for description.

The dehumidification and deodorization filter 32 serving as dehumidification and deodorization means removes the humidity and odor of the intake gas. The dehumidification and deodorization filter 32 is disposed on the first flow path 24. The gas passing through the first flow path 24 is dehumidified and deodorized by the dehumidification and deodorization filter 32. In such a manner, the first flow path 24 functions as a flow path capable of constantly guiding the gas, which is clean at a constant level, to the multi-array sensor 6. The clean gas that has passed through the first flow path 24 can be used as a zero-point gas of the sensor.

If the dehumidification and deodorization filter 32 is provided in such a manner, the detection target gas 23 can be used as a zero-point gas without preparing a standard gas.

For the dehumidification and deodorization filter 32, a material having a high humidity-removing effect for removing humidity and hydrophilic odor components, such as silica gel or molecular sieve, and a material having a high odor-adsorbing effect for removing odor components, such as activated carbon or zeolite, can be used in combination.

The deodorization filter 33 serving as deodorization means removes the odor of the intake gas. The deodorization filter 33 is disposed on the second flow path 25. The gas passing through the second flow path 25 is deodorized by the deodorization filter 33. In such a manner, the second flow path 25 functions as a flow path capable of guiding the gas, from which the odor components have been removed, to the multi-array sensor 6.

For the deodorization filter 33, a material having a high odor-adsorbing effect, such as activated carbon or zeolite, can be used to remove odor components.

The dehumidification and deodorization filter, the deodorization filter, or the like is not disposed on the third flow path 26, and the detection target gas 23 taken in from the outside is directly introduced into the third flow path 26. The third flow path 26 guides the detection target gas 23 for odor monitoring to the multi-array sensor 6 disposed on the fifth flow path 28.

The temperature and humidity sensor 30 is for detecting the temperature and humidity of the detection target gas 23. The temperature and humidity sensor 30 is disposed on the fourth flow path 27. The temperature and humidity information detected by the temperature and humidity sensor 30 is output to the arithmetic device 4.

The arithmetic device 4 corrects, on the basis of the temperature detected by the temperature and humidity sensor 30, the resonant frequency detected by each of QCMs 10a to 10f so as to cancel the resonant frequency change due to temperature. This makes it possible to detect the resonant frequency change without the effect of temperature. Note that in the following description the description of the correction using the temperature detected by the temperature and humidity sensor 30 will be omitted.

Further, the arithmetic device 4 corrects, on the basis of the humidity detected by the temperature and humidity sensor 30, the resonant frequency detected by each of the QCMs 10a to 10f. This will be described in detail later.

For example, a digital temperature and humidity sensor (model number: SHT21) manufactured by Sensirion AG can be used for the temperature and humidity sensor 30.

The multi-array sensor 6 includes a plurality of QCMs 10 as detection elements. In this embodiment, an example in which six QCMs are provided is given, but at least one QCM may suffice.

The multi-array sensor 6 includes a first QCM sensor element (hereinafter, referred to as a first QCM) 10a as a first detection element, a second QCM sensor element (hereinafter, referred to as a second QCM) 10b as a second detection element, a third QCM sensor element (hereinafter, referred to as a third QCM) 10c as a third detection element, a fourth QCM sensor element (hereinafter, referred to as a fourth QCM) 10d as a fourth detection element, a fifth QCM sensor element (hereinafter, referred to as a fifth QCM) 10e as a fifth detection element, and a sixth QCM sensor element (hereinafter, referred to as a sixth QCM) 10f as a sixth detection element.

The first QCM 10a, the second QCM 10b, the third QCM 10c, the fourth QCM 10d, the fifth QCM 10e, and the sixth QCM 10f each have a configuration including a crystal oscillator as an oscillator, and an adsorption film for adsorbing a specific gas, which is provided on the crystal oscillator. The first QCM 10a, the second QCM 10b, the third QCM 10c, the fourth QCM 10d, the fifth QCM 10e, and the sixth QCM 10f have the same basic structure and are different only in the type of the adsorption film. Hereinafter, if it is not necessary to distinguish between the first QCM 10a, the second QCM 10b, the third QCM 10c, the fourth QCM 10d, the fifth QCM 10e, and the sixth QCM 10f, they may be referred to as QCM(s) 10.

Figure 2:
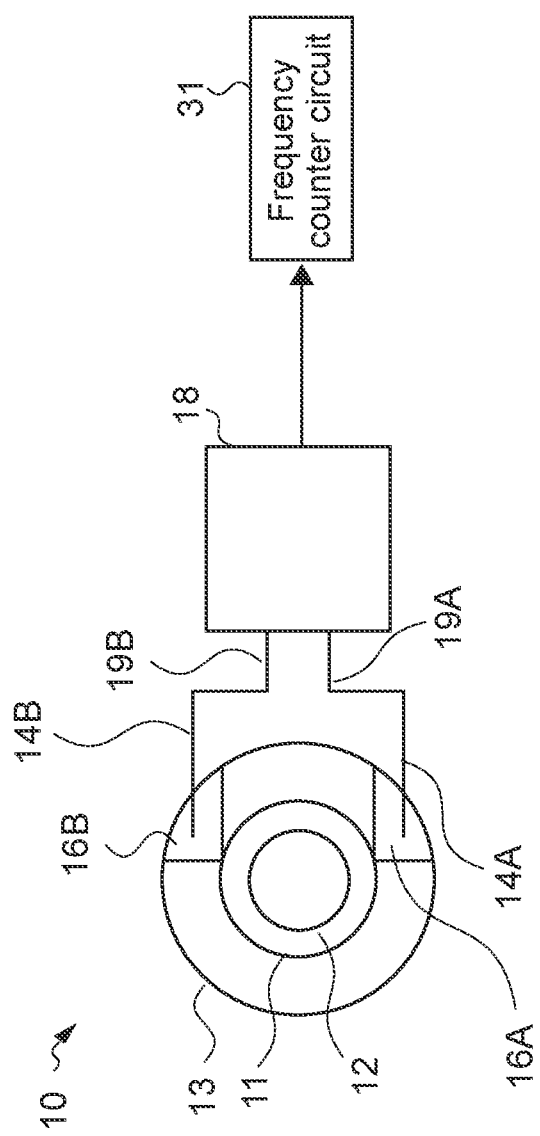
FIG. 2 is a front view of a QCM included in a gas sensor constituting a part of the gas detection system.

As shown in FIG. 2, the QCM 10 includes a crystal oscillator 13, an electrodes 11, an adsorption film 12, a lead land 16A, a lead land 16B, a lead 14A, a lead 14B, a pin terminal 19A, a pin terminal 19B, and a holder 18. The crystal oscillator 13 is an AT-cut quartz plate.

Since the resonant frequency of the crystal oscillator 13 of the QCM 10 decreases in proportion to the weight of the gas adsorbed on the adsorption film 12, it is possible to calculate a resonant frequency change amount for each QCM, and detect, on the basis of such a calculation result, whether or not the detection target gas contains a gas to be detected on the adsorption film 12.

In this embodiment, the crystal oscillator is used as the detection element, but the crystal oscillator is not limited thereto. For example, a ceramic oscillator, a surface acoustic wave element, a cantilever, a diaphragm, or the like may be used other than the crystal oscillator, and it can be applied as long as it can detect a physical change such as a weight increase or an expansion stress increase due to gas adsorption of the adsorption film and can convert the physical change into an electrical signal.

Hereinafter, the adsorption film provided to the first QCM 10a will be referred to as a first adsorption film 12a, the adsorption film provided to the second QCM 10b will be referred to as a second adsorption film 12b, the adsorption film provided to the third QCM 10c will be referred to as a third adsorption film 12c, the adsorption film provided to the fourth QCM 10d will be referred to as a fourth adsorption film 12d, the adsorption film provided to the fifth QCM 10e will be referred to as a fifth adsorption film 12e, and the adsorption film provided to the sixth QCM 10f will be referred to as a sixth adsorption film 12f.

The electrode 11 is formed on each of both surfaces of the crystal oscillator 13, and the adsorption film 12 is formed on the electrode 11 formed on one surface of the crystal oscillator 13. The lead land 16A is formed integrally with the electrode 11 formed on one surface, and the lead land 16B is formed integrally with the electrode 11 formed on the other surface.

The lead 14A and the lead 14B are made of a metallic spring material and are disposed parallel to each other.

One end of the lead 14A is electrically connected to the electrode 11 formed on one surface through the lead land 16A, and the other end thereof is connected to the pin terminal 19A. One end of the lead 14B is electrically connected to the electrode 11 formed on the other surface through the lead land 16B, and the other end thereof is connected to the pin terminal 19B.

The pin terminal 19A and the pin terminal 19B are supported by the holder 18 provided on the substrate, and the crystal oscillator 13 is supported vibratingly by the holder 18.

The pin terminals 19A and 19B of the QCM 10 are connected to an oscillator circuit (not shown), and a drive voltage is applied to the QCM 10. When a drive voltage is applied to the QCM 10, the crystal oscillator 13 oscillates at a particular resonant frequency.

The adsorption film 12 adsorbs the gas and thus changes the mass, and the oscillation frequency of the crystal oscillator 13 decreases in accordance with the amount of adsorption. In such a manner, in the QCM 10, the gas detection is performed with the weight change due to gas adsorption being as a resonant frequency change. In addition, the gas concentration can be quantified in accordance with the amount of change in frequency.

The first QCM 10a, the second QCM 10b, the third QCM 10c, the fourth QCM 10d, the fifth QCM 10e, and the sixth QCM 10f are respectively connected to the first frequency counter circuit 31a, the second frequency counter circuit 31b, the third frequency counter circuit 31c, the fourth frequency counter circuit 31d, the fifth frequency counter circuit 31e, and the sixth frequency counter circuit 31f, each of which is a resonant frequency measurement unit.

The frequency counter circuit 31 measures a resonant frequency of the adsorption film 12 of the QCM 10. The electrical signal of the resonant frequency measured by each of the frequency counter circuits 31a to 31f is output to the arithmetic device 4.

Each of the first adsorption film 12a, the second adsorption film 12b, the third adsorption film 12c, the fourth adsorption film 12d, the fifth adsorption film 12e, and the sixth adsorption film 12f is of a different type.

In this embodiment, the first adsorption film 12a is an adsorption film made of a fluorine-containing polymer material (product name: FS-2040 (manufactured by Fluoro Technology)) and selectively adsorbs a lipophilic gas.

The second adsorption film 12b is an adsorption film made of a fluorine-containing amphipathic polymer material (product name: FS-6130 (manufactured by Fluoro Technology)) and selectively adsorbs a hydrophilic gas and a lipophilic gas.

The third adsorption film 12c is an adsorption film made of an oily hydrocarbon material Squalene (manufactured by Fujifilm Wako Pure Chemical Corporation) and selectively adsorbs a hydrophilic gas and a lipophilic gas.

The fourth adsorption film 12d is an adsorption film made of Cellulose Acetate Propionate (CAP-482, manufactured by Eastman) and selectively adsorbs a hydrophilic gas.

The fifth adsorption film 12e is an adsorption film made of Poly(3, 4-ethylenedioxythiophene) (product name: PEDOT687316, manufactured by Ardrich) and selectively adsorbs a hydrophilic gas.

The sixth adsorption film 12f is an adsorption film made of cellulose, Cellulose Acetate Butyrate (CAB-553, manufactured by Eastman) and selectively adsorbs a hydrophilic gas.

(A), (B), and (C) of FIG. 3 are diagrams for describing resonant frequency changes associated with the humidity change of the gas detected by the first QCM 10a, the second QCM 10b, and the third QCM 10c, respectively.

(A), (B), and (C) of FIG. 4 are diagrams for describing resonant frequency changes associated with the humidity change of the gas detected by the fourth QCM 10d, the fifth QCM 10e, and the sixth QCM 10f, respectively.

All the diagrams show an approximate line of the measured resonant frequency plotted with a changed humidity of the gas reaching each QCM.

As shown in FIGS. 3 and 4, since the types of the adsorption films 12 are different from each other, the resonance frequencies are different from each other. In any of the QCMs 10a to 10f, however, the resonance frequencies substantially linearly vary with the humidity change of the gas.

The arithmetic device 4 includes an acquisition unit 41, a calculation unit 42, a determination unit 43, an output unit 44, a storage unit 45, and a recognition unit 46.

The storage unit 45 stores in advance the resonant frequency detected by each of the QCMs 10a to 10f in the initial state at which the zero-point gas has arrived, and the resonant frequency change amount associated with the humidity change.

The resonant frequency detected by the QCM 10 in the initial state is a resonant frequency detected when a clean gas (zero-point gas), which is obtained after outside gas passes through the first flow path 24 to be dehumidified and deodorized, arrives at the QCM 10 in the initial state having no film deterioration. Such a resonant frequency is acquired in advance for each of the QCMs 10a to 10f and stored.

The resonant frequency change amount associated with the humidity change is a resonant frequency change amount in the QCM 10 with respect to the change of a relative humidity of 1%. Such a resonant frequency change amount is calculated in advance on the basis of: a resonant frequency detected when the zero-point gas, which is obtained after outside gas passes through the first flow path 24, arrives at the QCM 10 in the initial state; a resonant frequency detected when the deodorized gas, which is obtained after outside gas passes through the second flow path 25, arrives at the QCM 10 in the initial state; and the humidity information detected by the temperature and humidity sensor 30 when outside gas passes through the fourth flow path 27. Such a resonant frequency change amount is calculated in advance for each of the QCMs 10a to 10f and stored.

The storage unit 45 stores in time series a correction coefficient Rc calculated by the calculation unit 42, which will be described later, in association with the calculated date and time information. The calculation of the correction coefficient Rc may be performed periodically or may be performed at any timing by the user.

Further, the storage unit 45 stores in advance reference detection patterns when various gases are detected by the multi-array sensor 6 for each different type of gas.

The recognition unit 46 compares a detection pattern corrected using the correction coefficient by the calculation unit 42, which will be described later, with the reference detection pattern stored in advance in the storage unit 45, and recognizes the presence or absence of gas and the type of gas by pattern recognition of machine learning.

The acquisition unit 41 acquires the resonant frequency of each of the QCMs 10a to 10f detected by each of the frequency counter circuits 31a to 31f, and the temperature and humidity information detected by the temperature and humidity sensor 30.

More specifically, the acquisition unit 41 acquires the resonant frequency detected by each of the QCMs 10a to 10f in the degraded state at which a so-called zero-point gas has arrived, the zero-point gas being obtained after the detection target gas 23 passes through the first flow path 24 to be dehumidified and deodorized.

The acquisition unit 41 acquires the resonant frequency detected by each of the QCMs 10a to 10f in the degraded state at which the deodorized gas has arrived, the deodorized gas being obtained after the detection target gas 23 passes through the second flow path 25.

The acquisition unit 41 acquires the resonant frequency detected by each of the QCMs 10a to 10f in the degraded state at which the detection target gas 23 having passed through the third flow path 26 has arrived.

The acquisition unit 41 acquires the temperature and humidity information detected by the temperature and humidity sensor 30 on the fourth flow path 27.

When calculating the correction coefficient Rc to be described later, the calculation unit 42 calculates the resonant frequency change amount of each of the QCMs 10a to 10f with respect to the change of a relative humidity of 1% on the basis of the resonant frequencies detected by the respective QCMs 10a to 10f at which the gas having passed through the first flow path 24 and the second flow path 25 has arrived, and the humidity information detected by the temperature and humidity sensor 30.

When calculating the correction coefficient Rc, the calculation unit 42 acquires the resonant frequency change amount of each of the QCMs 10a to 10f in the initial state with respect to the humidity change, which is stored in the storage unit 45.

The calculation unit 42 calculates, using the following equation, the ratio Rc between a resonant frequency change amount $\Delta F(a)$ of each of the QCMs 10a to 10f in the degraded state with respect to the humidity change and a resonant frequency change amount $\Delta F(0)$ of each of the QCMs 10a to 10f in the initial state with respect to the humidity change, which is stored in the storage unit 45. The ratio Rc is used as a correction coefficient.

$$Rc = \Delta F(0)/\Delta F(a)$$

where $\Delta F(a)$ is a resonant frequency change (Hz) with respect to the change of a relative humidity of 1% in the adsorption film in the degraded state, and $\Delta F(0)$ is a resonant frequency change (Hz) with respect to the change of a relative humidity of 1% in the adsorption film in the initial state.

The calculation of the correction coefficient Rc is performed for each of the QCMs 10a to 10f. The calculated correction coefficient Rc is stored in the storage unit 45.

When not calculating the correction coefficient Rc, the calculation unit 42 acquires the latest correction coefficient Rc stored in the storage unit 45.

The calculation unit 42 calculates the resonant frequency change amount on the basis of the resonant frequency detected by each of the QCMs 10a to 10f in the degraded state at which the detection target gas 23 having passed through the third flow path 26 has arrived.

Furthermore, the calculation unit 42 corrects, using the correction coefficient Rc, the resonant frequency change amount of each of the QCMs 10a to 10f in the degraded state at which the detection target gas 23 having passed through the third flow path 26 has arrived.

More specifically, the calculation unit 42 corrects the resonant frequency change amount by multiplying the value of the resonant frequency change amount of each of the QCMs 10a to 10f in the degraded state at which the detection target gas 23 having passed through the third flow path 26 has arrived, by the correction coefficient Rc. Thus, it is possible to correct the resonant frequency change amount to be an output value at substantially the same sensor sensitivity level as that in the initial state. A specific example will be described later with reference to FIG. 5.

As described above, the detection results in the respective QCMs 10a to 10f, at which the gas having passed through the first flow path 24 and the second flow path 25 has arrived, are used for calculating the correction coefficient Rc.

The calculation of the correction coefficient Rc and the correction of the resonant frequency change amount using the correction coefficient Rc can be the step of calibrating the output value of the QCM in the degraded state to be an output value at substantially the same sensitivity level as that in the initial state.

The calculation of the correction coefficient Rc in the calibration step does not have to be performed for each gas detection in the gas sensor 2, and may be configured to be performed automatically every predetermined period, for example, every month, or performed by a user at any timing.

Subsequently, the correction coefficient Rc in each of the QCMs 10a to 10f calculated in the calibration step is stored in the storage unit 45, and the correction of the resonant frequency change amount is performed using the correction coefficient Rc most recently calculated and stored in the storage unit 45 until the next correction coefficient Rc is calculated.

Thus, in the gas detection by the gas detection system 1 in a period in which the calculation of the correction coefficient Rc is not performed, it is not necessary to detect the gas having passed through the first flow path 24 and the second flow path 25. As described above, the first flow path 24 and the second flow path 25 can be used for the calibration step.

The determination unit 43 determines the lifetime of the QCM 10 on the basis of the difference between the resonant frequency detected by the QCM 10 in the degraded state at which the zero-point gas having passed through the first flow path 24 has arrived, and the resonant frequency detected by the QCM 10 in the initial state at which the zero-point gas having passed through the first flow path 24 has arrived, which is acquired in advance and stored in the storage unit 45.

When the adsorption film 12 reaches the end of its lifetime due to deterioration over time, the QCM 10 hardly has stable oscillation characteristics. In such a state, even if the calculation of the resonant frequency change amount using the correction coefficient is performed, it is difficult to sufficiently correct the resonant frequency change amount.

In this embodiment, when the difference between the resonant frequency detected by the QCM 10 in the degraded state at which the zero-point gas having passed through the first flow path 24 has arrived, and the resonant frequency detected by the QCM 10 in the initial state at which the zero-point gas having passed through the first flow path 24 has arrived, which is acquired in advance and stored in the storage unit 45, exceeds a threshold value, it is possible to determine that the QCM 10 has reached the end of its lifetime. The threshold value used for the lifetime determination varies depending on the resonant frequency band of the QCM and is individually set according to the type of the adsorption film 12.

Here, the difference between the resonant frequency detected by the QCM 10 in the degraded state at which the zero-point gas has arrived and the resonant frequency detected by the QCM 10 in the initial state at which the zero-point gas has arrived is a frequency accumulated due to deterioration over time. From such a difference in resonant frequency, a negative resistance of the QCM 10 in the degraded state can be estimated. If the negative resistance of the oscillator circuit is sufficiently larger than an equivalent series resonant resistance of the crystal oscillator, stable oscillation characteristics can be obtained, otherwise stable oscillation characteristics cannot be obtained.

Figure 8:
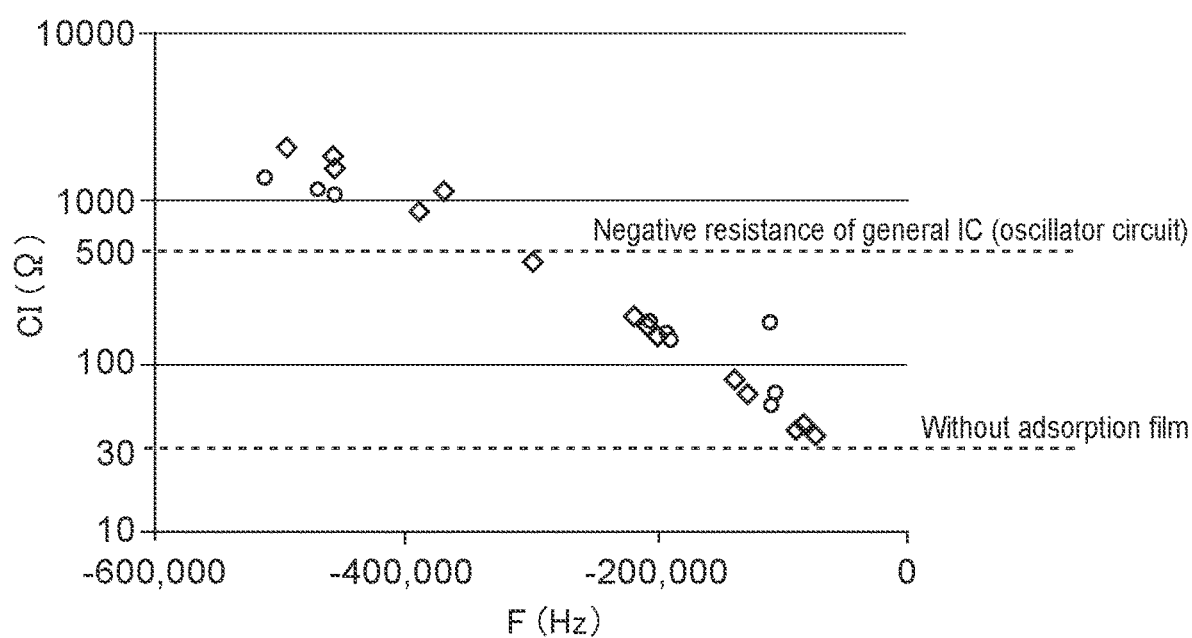
FIG. 8 is for describing the QCM lifetime determination.

FIG. 8 shows, as an example, the relationship between the negative resistance and the resonant frequency of the QCMs including two different types of adsorption films and having a resonant frequency of 32 MHz. Circle plots and diamond plots show the QCMs respectively including different types of adsorption films.

As shown in FIG. 8, the negative resistance varies linearly with the change in resonant frequency. In the example shown in FIG. 8, when the negative resistance of the QCM exceeds 500Ω, the QCM fails to stably oscillate. Assuming that the end of the lifetime comes when the negative resistance exceeds 500Ω, if the difference between the resonant frequencies in the degraded state and in the initial state is larger than 200,000 Hz, which is the threshold value, the QCM is determined to have reached the end of the lifetime.

In such a manner, in the QCM associated with resonant vibration, the resonant frequency at which oscillation cannot be stably performed can be estimated from the negative resistance, and the lifetime of the QCM can be determined from the estimated negative resistance. Thus, if it is determined that the end of the lifetime has come, it is possible to promptly replace the QCM or the gas sensor, maintain substantially the same level as the sensitivity level in the initial state from the start of use of the QCM or the gas sensor to the replacement thereof, and stably perform the gas detection.

The output unit 44 outputs, to the display device 5, the resonant frequency change amounts of the respective QCMs 10a to 10f calculated by the calculation unit 42 using the correction coefficients, the discrimination result of the detected gas recognized by the recognition unit 46, the quantitative analysis result of the detected gas, and the life determination result determined by the determination unit 43.

The display device 5 includes a display unit and displays, on the display unit, the corrected resonant frequency change amounts of the respective QCMs 10a to 10f output from the arithmetic device 4, the discrimination result of the detected gas, the gas concentration, the lifetime determination result, etc. The user can understand the type and concentration of the detected gas and the replacement timing of the QCM or the gas sensor by checking the display unit.

Next, the arithmetic method relating to the calculation of the correction coefficient performed by the arithmetic device 4 and the calculation of the resonant frequency change amount using the correction coefficient will be described with reference to the flowchart of FIG. 6.

Figure 6:
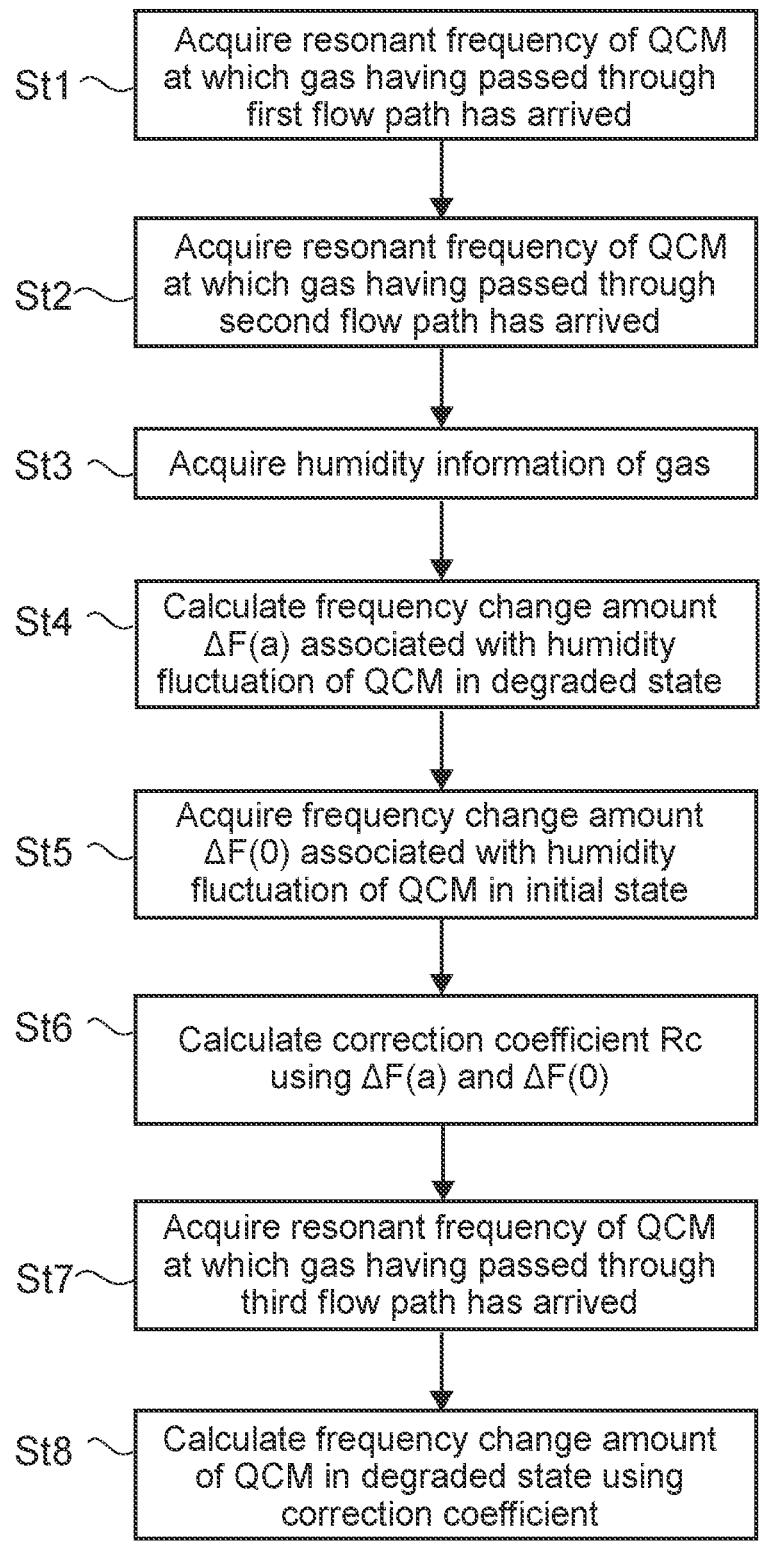
FIG. 6 is a flowchart for describing an arithmetic method relating to gas detection in an arithmetic device of the gas detection system according to the first embodiment.

As shown in FIG. 6, the acquisition unit 41 acquires the electric signal of the resonant frequency detected by each of the QCMs 10a to 10f in the degraded state at which the gas having passed through the first flow path 24 has arrived, which is output from each of the frequency counter circuits 31a to 31f (St1).

Next, the acquisition unit 41 acquires the electric signal of the resonant frequency detected by each of the QCMs 10a to 10f in the degraded state at which the gas having passed through the second flow path 25 has arrived, which is output from each of the frequency counter circuits 31a to 31f (St2).

Next, the acquisition unit 41 acquires humidity information detected by the temperature and humidity sensor 30 (St3).

Next, the calculation unit 42 calculates the resonant frequency change amount ΔF(a) of each of the QCMs 10a to 10f in the degraded state with respect to the change of a relative humidity of 1% by using the resonant frequency serving as a detection result of the gas passing through the first flow path 24, which is obtained in St1, the resonant frequency serving as a detection result of the gas passing through the second flow path 25, which is acquired in St2, and the humidity information detected by the temperature and humidity sensor 30 (St4).

The gas having passed through the first flow path 24 and the gas having passed through the second flow path 25 are both the deodorized gases from which odor components are removed. The gas having passed through the first flow path 24 is a dehumidified gas from which moisture is removed, and the gas having passed through the second flow path 25 is a gas that is not dehumidified, and both of them are different in humidity. Therefore, it is possible to calculate the resonant frequency change amount of each of the QCMs 10a to 10f in the degraded state with respect to the change of a relative humidity of 1% on the basis of the resonant frequency obtained in St1, the resonant frequency obtained in St2, and the humidity information obtained in St3.

Next, the calculation unit 42 acquires the resonant frequency change amount ΔF(0) of each of the QCMs 10a to 10f in the initial state with respect to the humidity change, which is stored in advance in the storage unit 45 (St5).

Next, the ratio Rc between the resonant frequency change amount ΔF(a) calculated in St4 and the resonant frequency change amount ΔF(0) acquired in St5 is calculated as a correction coefficient (St6). The correction coefficient Rc is calculated for each of the QCMs 10a to 10f.

Next, the acquisition unit 41 acquires the resonant frequency detected by each of the QCMs 10a to 10f in the degraded state at which the gas having passed through the third flow path 26 has arrived, which is output from each of the frequency counter circuits 31a to 31f (St7).

Next, the resonant frequency change amount of each of the QCMs 10a to 10f in the degraded state is calculated using the resonant frequency acquired in St7, and the above resonant frequency change amount is multiplied by the correction coefficient Rc calculated in St6, so that the resonant frequency change amount is corrected (St8).

The resonant frequency change amount calculated and corrected using the correction coefficient Rc is substantially the same as the value detected at the same sensitivity level as in the gas sensor 2 in the initial state.

Hereinafter, the fact that the resonant frequency change amount calculated using the correction coefficient Rc substantially coincides with the resonant frequency change amount when detected by the gas sensor 2 in the initial state will be described with reference to FIG. 5.

In FIG. 5, the correction coefficient Rc is obtained by the ratio between the resonant frequency change amount ΔF(0) associated with the humidity fluctuation in the initial state and the resonant frequency change amount ΔF(a) associated with the humidity fluctuation after deterioration over time (degraded state).

The resonant frequency change amount of ethanol (100 ppm) in the initial state is a resonant frequency change amount of the QCM 10 in the initial state when ethanol is detected. The resonant frequency change amount of ethanol (100 ppm) after deterioration over time (degraded state) is a resonant frequency change amount of the QCM 10 in the degraded state when ethanol is detected.

The resonant frequency change amount after correction is a value obtained by multiplying the resonant frequency change amount of ethanol (100 ppm) after deterioration over time (degraded state) by the correction coefficient Rc.

The output coincidence rate indicates the coincidence rate of the corrected resonant frequency change amount to the resonant frequency change amount of the QCM 10 in the initial state when ethanol is detected.

Here, in the adsorption film 12 of the QCM 10 in the degraded state, some of the adsorption sites are occupied by the odor components that are not desorbed, and the adsorption is allowed only on the empty adsorption sites. For this reason, the resonant frequency change amount due to adsorption in the QCM 10 in the degraded state is smaller than that in the QCM 10 in the initial state.

The resonant frequency change associated with the humidity change in each QCM is substantially linear as shown in FIGS. 3 and 4 described above. It is possible to obtain the resonant frequency change amount of the QCM with respect to the change of a relative humidity of 1% from the resonant frequencies detected by the QCMs at which at least two gases having different humidities have arrived.

Therefore, the ratio of adsorption sites capable of adsorption on the surface of the adsorption film can be estimated from the ratio between the resonant frequency change amount of the QCM in the initial state with respect to the change of a relative humidity of 1% and the resonant frequency change amount of the QCM in the degraded state with respect to the change of a relative humidity of 1%. Subsequently, using such a ratio, the resonant frequency change amount detected by the QCM in the degraded state is corrected to perform calibration, so that it is possible to convert it into the resonant frequency change amount detected at substantially the same sensitivity level as that of the QCM in the initial state.

As shown in FIG. 5, in the first QCM 10a, a value (resonant frequency change amount after correction) obtained by correcting the resonant frequency change amount detected by the first QCM 10a in the degraded state, 9 Hz, using the correction coefficient Rc is 22 Hz. This value is substantially the same as the resonant frequency change amount of ethanol by the first QCM 10a in the initial state, 20 Hz. The coincidence rate of the output values is 108%.

Similarly, as shown in FIG. 5, in the second QCM 10b, a value (resonant frequency change amount after correction) obtained by correcting the resonant frequency change amount detected by the second QCM 10b in the degraded state, 55 Hz, using the correction coefficient Rc is 72 Hz. This value is substantially the same as the resonant frequency change amount of ethanol by the second QCM 10b in the initial state, 70 Hz. The coincidence rate of the output values is 103%.

In the third QCM 10c, a value (resonant frequency change amount after correction) obtained by correcting the resonant frequency change amount detected by the third QCM 10c in the degraded state, 95 Hz, using the correction coefficient Rc is 191 Hz. This value is substantially the same as the resonant frequency change amount of ethanol by the third QCM 10c in the initial state, 200 Hz. The coincidence rate of the output values is 95%.

In the fourth QCM 10d, a value (resonant frequency change amount after correction) obtained by correcting the resonant frequency change amount detected by the fourth QCM 10d in the degraded state, 145 Hz, using the correction coefficient Rc is 202 Hz. This value is substantially the same as the resonant frequency change amount of ethanol by the fourth QCM 10d in the initial state, 210 Hz. The coincidence rate of the output values is 96%.

In the fifth QCM 10e, a value (resonant frequency change amount after correction) obtained by correcting the resonant frequency change amount detected by the fifth QCM 10e in the degraded state, 176 Hz, using the correction coefficient Rc is 363 Hz. This value is substantially the same as the resonant frequency change amount of ethanol by the fifth QCM 10e in the initial state, 350 Hz. The coincidence rate of the output values is 104%.

In the sixth QCM 10f, a value (resonant frequency change amount after correction) obtained by correcting the resonant frequency change amount detected by the sixth QCM 10f in the degraded state, 64 Hz, using the correction coefficient Rc is 118 Hz. This value is substantially the same as the resonant frequency change amount of ethanol by the sixth QCM 10f in the initial state, 120 Hz. The coincidence rate of the output values is 99%.

In such a manner, the resonant frequency change amount corrected with the correction coefficient Rc is a value detected at substantially the same sensitivity level as that of the QCM 10 in the initial state.

Further, as described above, when the adsorption film 12 reaches the end of its lifetime due to deterioration over time, the QCM 10 fails to stably oscillate. Such a determination on the end of lifetime that the QCM 10 fails to stably oscillate can be performed as described below, and it is possible to predict the lifetime of the gas sensor. Hereinafter, the description will be given with reference to FIG. 7.

Figure 7:
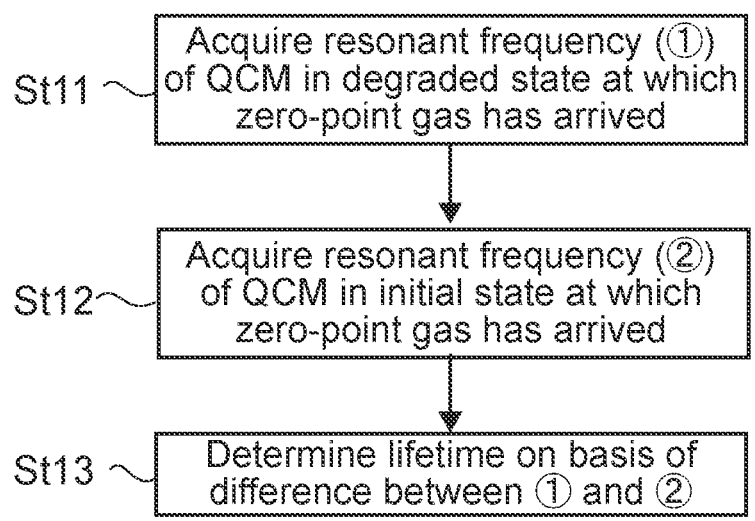
FIG. 7 is a flowchart for describing an arithmetic method relating to QCM lifetime determination in the arithmetic device of the gas detection system according to the first embodiment.

FIG. 7 is a flowchart for describing an arithmetic method relating to the QCM lifetime determination.

As shown in FIG. 7, the acquisition unit 41 acquires the resonant frequency of the QCM 10 in the degraded state at which the zero-point gas has arrived, which is detected by the frequency counter circuit 31 (St11).

Next, the determination unit 43 acquires the resonant frequency of the QCM 10 in the initial state at which the zero-point gas has arrived, which is stored in the storage unit 45 in advance (St12).

Next, the determination unit 43 determines the lifetime of the QCM 10 on the basis of the difference between the resonant frequency of the QCM 10 in the degraded state acquired in St11 and the resonant frequency of the QCM 10 in the initial state acquired in St12 (St13). Specifically, when the calculated difference is larger than a threshold value, it is determined that the QCM 10 has reached the end of the lifetime. When the difference is equal to or smaller than the threshold value, it is determined that the QCM 10 has not yet reached the end of the lifetime.

As described above, in this embodiment, the amount of adsorption sites capable of adsorption on the surface of the adsorption film can be estimated from the ratio between the resonant frequency change amount of the QCM in the initial state with respect to the change of a relative humidity of 1% and the resonant frequency change amount of the QCM in the degraded state with respect to the change of a relative humidity of 1%. Using such a ratio, it is possible to perform calibration of the output value of the gas sensor 2 by correcting the resonant frequency change amount detected by the QCM in the degraded state. Thus, it is possible to convert the resonant frequency change amount detected by the QCM in the degraded state into a resonant frequency change amount detected at substantially the same sensitivity level as that of the QCM in the initial state. This makes it possible to easily correct deterioration over time of the detection element and to perform detection at a stable sensitivity level.

Furthermore, it is possible to estimate the lifetime of the sensor, which cannot be corrected by the output correction using the correction coefficient Rc, from the degree of deterioration due to deterioration over time. Therefore, if it is determined that the end of the lifetime has come, it is possible to promptly replace the QCM or the gas sensor, maintain substantially the same level as the sensitivity level in the initial state from the start of use of the QCM or the gas sensor to the replacement thereof, and stably perform the gas detection.

Second Embodiment

In the first embodiment, an example has been described in which the first flow path including the dehumidification and deodorization filter and the second flow path including the deodorization filter are provided to obtain a correction coefficient for calibrating the output value of the gas sensor 2, but the present invention is not limited thereto. The correction coefficient may be obtained by using at least two kinds of standard gases having different humidities without providing a dehumidification and deodorization filter or a deodorization filter. Hereinafter, description will be given with reference to FIG. 9. In the following description, the same constituent elements as those described above will be denoted by the same reference symbols, and description thereof will be omitted.

Figure 9:
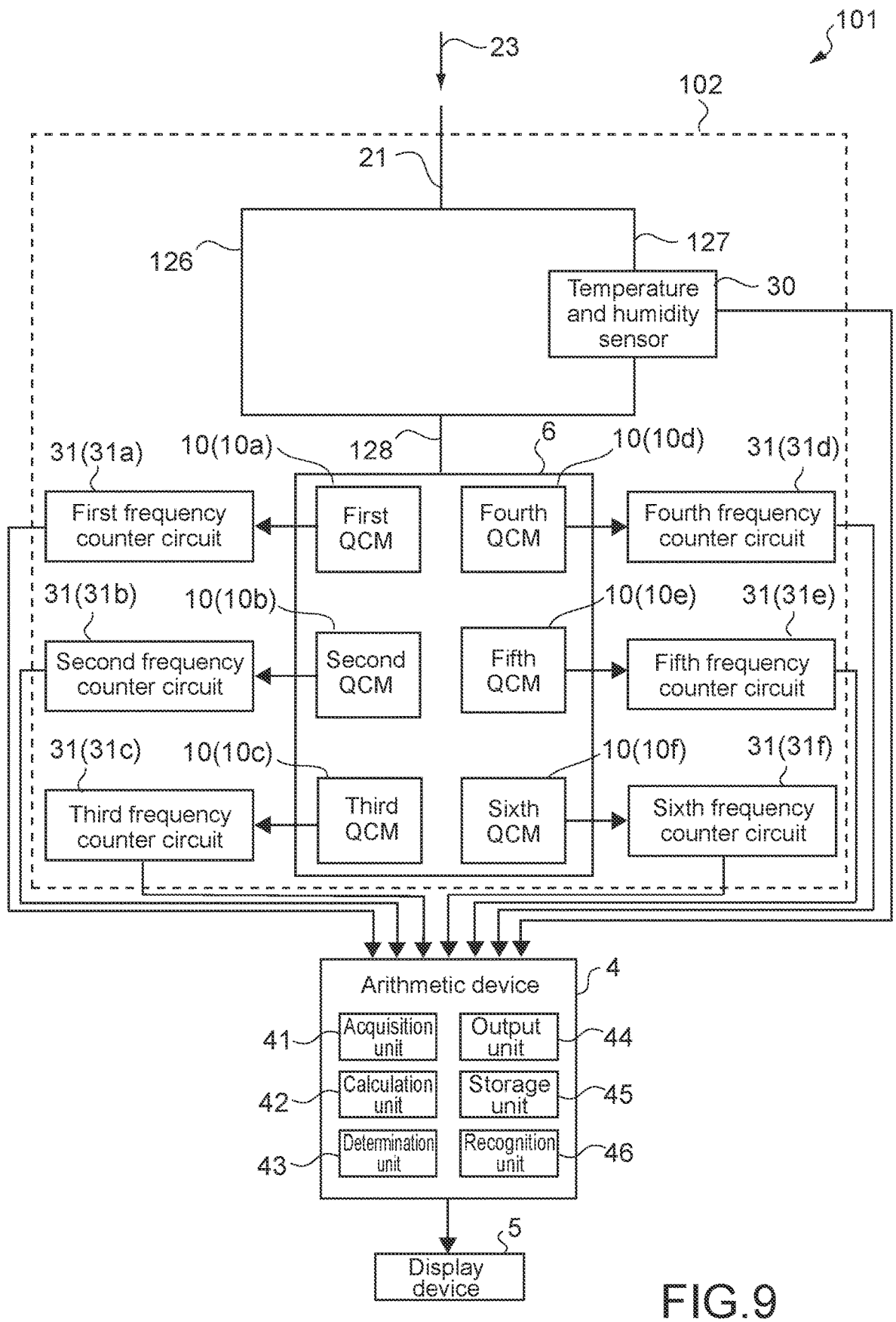
FIG. 9 is a schematic diagram showing a configuration of a gas detection system according to a second embodiment of the present invention.

FIG. 9 is a schematic diagram of a gas detection system 101 according to a second embodiment.

As shown in FIG. 9, the gas detection system 101 includes a gas sensor 102, an arithmetic device 4, and a display device 5.

As shown in FIG. 9, the gas sensor 102 includes an intake port 21, a monitoring flow path 126, a temperature and humidity detection flow path 127, and a flow path 128 for a multi-array sensor that is a single flow path into which gas passing through the two flow paths 126 and 127 flows.

The intake port 21 takes in the detection target gas 23 from the outside.

The gas taken in from the intake port 21 can be guided to the two flow paths 126 and 127.

Each of the flow paths 126 and 127 is configured such that the detection target gas 23 can be guided to the multi-array sensor 6 disposed on the flow path 128.

It is possible to introduce the gas into each of the flow paths 126 and 127 mechanically at a constant flow rate using a fan, a pump, or the like (not shown). This makes it possible to cancel a disturbance factor caused by a pressure change due to a difference in flow rate or the like. Further, a valve (not shown) is provided in each flow path, and the presence or absence of introduction of gas from the outside to each flow path can be controlled by opening or closing the valve.

As shown in FIG. 9, the gas sensor 102 includes a temperature and humidity sensor 30, the multi-array sensor 6, a first frequency counter circuit 31*a*, a second frequency counter circuit 31*b*, a third frequency counter circuit 31*c*, a fourth frequency counter circuit 31*d*, a fifth frequency counter circuit 31*e*, and a sixth frequency counter circuit 31*f*.

In the gas detection system 101, a correction coefficient Rc for calibrating the output value of the gas sensor 102 can be obtained by using a first standard gas and a second standard gas having no odor components and having different humidities. The first standard gas is a zero-point gas. The first and second standard gases do not contain odor components.

The storage unit 45 of the arithmetic device 4 stores in advance a resonant frequency detected by each of QCMs 10*a* to 10*f* in the initial state, and a resonant frequency change amount associated with the change of a relative humidity of 1%.

The resonant frequency detected by each of the QCMs 10*a* to 10*f* in the initial state is a resonant frequency detected when the first standard gas passes through the monitoring flow path 126 and arrives at each of the QCMs 10*a* to 10*f* in the initial state, and is stored in advance in the storage unit 45.

The resonant frequency change amount associated with the humidity change is a resonant frequency change amount in each QCM 10 with respect to the change of a relative humidity of 1%. Such a resonant frequency change amount is calculated in advance on the basis of: a resonant frequency detected when the first standard gas having passed through the monitoring flow path 126 arrives at each of the QCMs 10*a* to 10*f* in the initial state; a resonant frequency detected when the second standard gas having passing through the monitoring flow path 126 arrives at each of the QCMs 10*a* to 10*f* in the initial state; and the humidity information detected by the temperature and humidity sensor 30 when the first and second standard gases pass through the temperature and humidity detection flow path 127. Note that if the humidities of the first and second standard gases are known, the humidity information of the temperature and humidity sensor 30 may not be used.

The storage unit 45 stores in time series a correction coefficient Rc calculated by the calculation unit 42, which will be described later.

Further, the storage unit 45 stores in advance reference detection patterns when various gases are detected by the multi-array sensor 6 for each different type of gas.

The configuration of the recognition unit 46 is the same as that of the first embodiment.

The acquisition unit 41 acquires the electric signal of the resonant frequency of each of the QCMs 10*a* to 10*f*, which is output from each of the frequency counter circuits 31*a* to 31*f*, and acquires the temperature and humidity information detected by the temperature and humidity sensor 30.

More particularly, the acquisition unit 41 acquires the resonant frequency detected by each of the QCMs 10*a* to 10*f* in the degraded state at which each of the first standard gas and the second standard gas has arrived.

The acquisition unit 41 acquires the resonant frequency detected by each of the QCMs 10*a* to 10*f* in the degraded state at which the detection target gas 23 having passed through the monitor flow path 126 has arrived.

The acquisition unit 41 acquires the temperature and humidity information detected by the temperature and humidity sensor 30 on the temperature and humidity detection flow path 127.

The calculation unit 42 calculates a resonant frequency change amount ΔF(a) of each QCM 10 in the degraded state with respect to the change of a relative humidity of 1% on the basis of the resonant frequencies detected when each of the first standard gas and the second standard gas having passed through the monitoring flow path 126 arrives at the QCMs 10*a* to 10*f* in the degraded state, and the humidity information detected by the temperature and humidity sensor 30 when the first and second standard gases pass through the temperature and humidity detection flow path 127. Note that if the humidities of the first and second standard gases are known, the humidity information by the temperature and humidity sensor 30 may not be used.

The calculation unit 42 acquires a resonant frequency change amount ΔF(0) of each of the QCMs 10*a* to 10*f* in the initial state with respect to the humidity change, which is stored in advance in the storage unit 45.

The calculation unit 42 calculates, using the following equation, the ratio Rc between the resonant frequency change amount ΔF(a) of each of the QCMs 10*a* to 10*f* in the degraded state with respect to the humidity change and the resonant frequency change amount ΔF(0) of each of the QCMs 10*a* to 10*f* in the initial state with respect to the humidity change, which is stored in the storage unit 45. The ratio Rc is used as a correction coefficient.

$$Rc = \Delta F(0)/\Delta F(a)$$

where ΔF(a) is a resonant frequency change (Hz) with respect to the change of a relative humidity of 1% in the QCM in the degraded state, and ΔF(0) is a resonant frequency change (Hz) with respect to the change of a relative humidity of 1% in the QCM in the initial state.

The calculation of the correction coefficient is performed for each of the QCMs 10*a* to 10*f*.

The calculation unit 42 calculates the resonant frequency change amount on the basis of the resonant frequency detected by each of the QCMs 10*a* to 10*f* in the degraded state at which the detection target gas 23 having passed through the monitoring flow path 126 has arrived.

Furthermore, the calculation unit 42 corrects, using the correction coefficient Rc, the resonant frequency change amount of each of the QCMs 10*a* to 10*f* in the degraded state at which the detection target gas 23 having passed through the monitoring flow path 126 has arrived, and calculates the resonant frequency change amount converted into the sensitivity level in the initial state.

More specifically, the calculation unit 42 calculates the resonant frequency change amount by multiplying the value of the resonant frequency change amount of each of the QCMs 10*a* to 10*f* in the degraded state at which the detection target gas 23 having passed through the monitoring flow path 126 has arrived, by the correction coefficient Rc. Thus, it is possible to correct the resonant frequency change amount to be an output value at substantially the same sensitivity level as that in the initial state.

Next, the arithmetic method for the resonant frequency change amount associated with the humidity change, which is used to calculate the correction coefficient by the arithmetic device 4, will be described with reference to the flowchart of FIG. 10. Such a calculation of the resonant frequency change amount is the same in the initial state and the degraded state.

Figure 10:
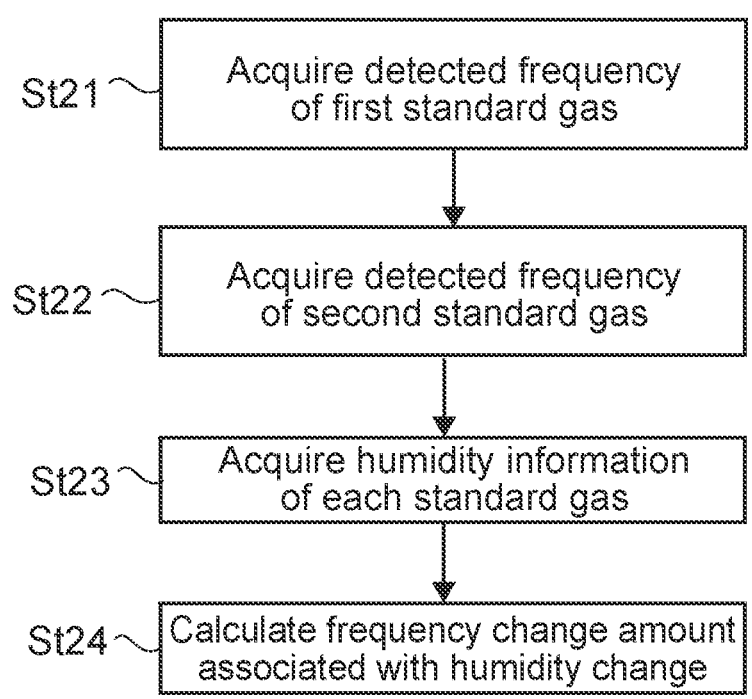
FIG. 10 is a flowchart for describing an arithmetic method relating to gas detection in an arithmetic device of the gas detection system according to the second embodiment.

As shown in FIG. 10, the acquisition unit 41 acquires the electric signal of the resonant frequency detected by each of the QCMs 10*a* to 10*f* at which the first standard gas having passed through the monitoring flow path 126 has arrived, which is output from each of the frequency counter circuits 31*a* to 31*f* (St21).

Next, the acquisition unit 41 acquires the electric signal of the resonant frequency detected by each of the QCMs 10*a* to 10*f* at which the second standard gas having passed through the monitoring flow path 126 has arrived, which is output from each of the frequency counter circuits 31*a* to 31*f* (St22).

Next, the acquisition unit 41 acquires the humidity information of each of the first and second standard gases detected by the temperature and humidity sensor 30 (St23).

Next, the calculation unit 42 calculates the resonant frequency change amount of each of the QCMs 10*a* to 10*f* with respect to the change of a relative humidity of 1% by using the resonant frequency serving as a detection result of the first standard gas passing through the monitoring flow path 126, which is acquired in St21, the resonant frequency serving as a detection result of the second standard gas passing through the monitoring flow path 126, which is acquired in St22, and the humidity information detected by the temperature and humidity sensor 30, which is acquired in St23 (St24).

In such a manner, the resonant frequency change amount of each of the QCMs 10*a* to 10*f* with respect to the change of a relative humidity of 1% for determining the correction coefficient Rc is calculated using the standard gases. The calculation of the correction coefficient, and the correction of the output level using the correction coefficient are similar to those in the first embodiment, and thus description thereof will be omitted here.

The calibration may be performed using the standard gases as in this embodiment. The detection of the gas can be performed at a stable sensitivity level as in the first embodiment.

Note that in the first embodiment the first flow path including the dehumidification and deodorization filter and the second flow path including the deodorization filter are provided, and thus it is unnecessary to prepare a standard gas in calculating the correction coefficient Rc.

In each of the above embodiments, the calibration is performed periodically or at any timing, and thus deterioration over time of the detection element is easily corrected, the sensitivity is constantly maintained at a constant level, and quantitative monitoring becomes possible.

Further, the sensor lifetime is estimated on the basis on the difference in resonant frequency between the QCM in the initial state and the QCM in the degraded state. Thus, the sensitivity is constantly maintained at a constant level, and quantitative monitoring becomes possible.

Further, since the gas sensor is constantly maintained at a constant level of sensitivity, it is possible to maintain the recognition accuracy of the presence or absence or the type of gas at a constant level. In other words, since the recognition unit 46 compares a detection pattern, which is corrected by the calculation unit 42 using the correction coefficient Rc, with the reference detection pattern, and determines the presence or absence or the type of gas by pattern recognition, it is possible to maintain the recognition accuracy of the presence or absence or the type of gas at a constant level. In such a manner, it is possible to suppress the deterioration of the sensitivity level of the QCM due to the deterioration over time from affecting the recognition accuracy in the pattern recognition.

Further, in each of the above embodiments, the process of calculating the resonant frequency change amount of the QCM in the degraded state with respect to the humidity change, and obtaining the correction coefficient Rc from the ratio between such a resonant frequency change amount and the resonant frequency change amount of the QCM in the initial state with respect to the humidity change can be performed in a few minutes.

Therefore, in this embodiment, the calibration can be performed in a much shorter time and the time efficiency is improved as compared with the case where the calibration is performed after performing refreshing by heat treatment required for several hours.

Note that the QCM may be refreshed by deodorization or heating of the flow path in which the QCM is disposed. Even in such a case, it is possible to detect gas at substantially the same sensitivity level as that in the initial state by obtaining the correction coefficient Rc and correcting the resonant frequency change as in this embodiment, even if odor components that cannot be removed by the refresh process remain on the adsorption film.

Of course the present invention is not limited to the above embodiments only and can be variously modified.

REFERENCE SIGNS LIST 1, 101 gas detection system
2, 102 gas sensor
4 arithmetic device
10a first QCM (detection element)
10b second QCM (detection element)
10c third QCM (detection element)
10d fourth QCM (detection element)
10e fifth QCM (detection element)
10f sixth QCM (detection element)
12 adsorption film
13 oscillator
23 detection target gas
24 first flow path
25 second flow path
26 third flow path
32 dehumidification and deodorization filter (dehumidification and deodorization means)
33 deodorization filter (deodorization means)
42 calculation unit
43 determination unit
45 storage unit

The invention claimed is:

1. A gas detection system comprising:
a gas sensor including a detection element that causes a resonant frequency change by adsorption of target gas; and
an arithmetic device including a calculator that calculates a correction coefficient on a basis of a resonant frequency change amount associated with a humidity change of the detection element in a degraded state and a resonant frequency change amount associated with a humidity change of the detection element in an initial state that was acquired in advance, and corrects the resonant frequency change amount associated with the humidity change of the detection element in the degraded state by using the correction coefficient,
wherein the resonant frequency change amount associated with the humidity change of the detection element in the initial state that was acquired in advance is a resonant frequency change amount associated with the humidity change of the detection element in the initial state that is calculated in advance on the basis of a first resonant frequency detected when a first gas that has been dehumidified and deodorized from the target gas arrives at the detection element in the initial state, a second resonant frequency detected when a second gas that has been deodorized without being dehumidified from the target gas arrives at the detection element in the initial state, and humidity information on the target gas detected by a humidity sensor.

2. The gas detection system according to claim 1, wherein the arithmetic device includes a storage that stores the resonant frequency change amount associated with the humidity change of the detection element in the initial state.

3. The gas detection system according to claim 2, wherein the storage stores the correction coefficient.

4. The gas detection system according to claim 2,
wherein the detection element is provided in a plurality,
wherein each of the plurality of detection elements includes an oscillator, and an adsorption film that is provided on the oscillator and adsorbs the target gas, the respective adsorption films of the plurality of detection elements being of mutually different types, and
wherein the storage stores the resonant frequency change amount associated with the humidity change of each of the plurality of detection elements in the initial state.

5. The gas detection system according to claim 1, wherein the arithmetic device includes a determiner that determines a lifetime of the detection element on a basis of a difference between a resonant frequency detected from the detection element in the degraded state to which the first gas has arrived, and a resonant frequency that was detected from the detection element in the initial state to which the first gas has arrived and that was acquired in advance.

6. The gas detection system according to claim 1, wherein the gas sensor includes:
a first flow path that includes a dehumidification and deodorization filter disposed therein and that guides the target gas having passed through the dehumidification and deodorization filter to the detection element,
a second flow path that includes a deodorization filter disposed therein and that guides the target gas having passed through the deodorization filter to the detection element, and
a third flow path that directly guides the target gas to the detection element.

7. An arithmetic method executed by a gas detection system, the gas detection system including a gas sensor including a detection element that causes a resonant frequency change by adsorption of target gas and an arithmetic device connected to the gas sensor, the method comprising:
calculating a resonant frequency change amount associated with a humidity change of the detection element in a degraded state;
calculating a correction coefficient on a basis of the resonant frequency change amount associated with the humidity change of the detection element in the degraded state and a resonant frequency change amount associated with a humidity change of the detection element in an initial state that was acquired in advance; and
correcting the resonant frequency change amount associated with the humidity change of the detection element in the degraded state by using the correction coefficient,
wherein the resonant frequency change amount associated with the humidity change of the detection element in the initial state that was acquired in advance is a resonant frequency change amount associated with the humidity change of the detection element in the initial state that is calculated in advance on the basis of a first resonant frequency detected when a first gas that has been dehumidified and deodorized from the target gas arrives at the detection element in the initial state, a second resonant frequency detected when a second gas that has been deodorized without being dehumidified from the target gas arrives at the detection element in the initial state, and humidity information on the target gas detected by a humidity sensor.

8. The arithmetic method according to claim 7, further comprising determining a lifetime of the detection element on a basis of a difference between the resonant frequency detected from the detection element in the degraded state to which the first gas has arrived, and the resonant frequency detected from the detection element in the initial state to which the first gas has arrived that was acquired in advance.

* * * * *